US011060147B2

(12) United States Patent
Ogier-Denis et al.

(10) Patent No.: US 11,060,147 B2
(45) Date of Patent: Jul. 13, 2021

(54) METHODS FOR PREDICTING ACUTE SEVERE COLITIS TREATMENT RESPONSE

(71) Applicants: INSERM (Institut National de la Sante et de la Recherche Medicale), Paris (FR); Universite Paris Diderot—Paris 7, Paris (FR); Assistance Publique-Hopitaux de Paris (APHP), Paris (FR); Universite de Bordeaux, Bordeaux (FR); CHU de Bordeaux, Talence (FR); Universite Paris XIII Paris-Nord, Villetaneuse (FR)

(72) Inventors: Eric Ogier-Denis, Paris (FR); Xavier Treton, Paris (FR); Yoram Bouhnik, Paris (FR); Ian Morilla, Villetaneuse (FR); David Laharie, Bordeaux (FR); Gilles Wainrib, Paris (FR); Mathieu Uzzan, Paris (FR)

(73) Assignees: INSERM (INSTITUT NATIONAL DE LA SANTE ET DE LA RECHERCHE MEDICALE), Paris (FR); UNIVERSITE DE PARIS, Paris (FR); ASSISTANCE PUBLIQUE-HOPPITAUX DE PARIS (APHP), Paris (FR); UNIVERSITE DE BORDEAUX, Bordeaux (FR); CHU DE BORDEAUX, Talence (FR); UNIVERSITE PARIS XIII PARIS-NORD, Villetaneuse (FR)

( * ) Notice: Subject to any disclaimer, the term of this patent is extended or adjusted under 35 U.S.C. 154(b) by 105 days.

(21) Appl. No.: 16/309,699

(22) PCT Filed: Jun. 14, 2017

(86) PCT No.: PCT/EP2017/064496
§ 371 (c)(1),
(2) Date: Dec. 13, 2018

(87) PCT Pub. No.: WO2017/216206
PCT Pub. Date: Dec. 21, 2017

(65) Prior Publication Data
US 2019/0136324 A1    May 9, 2019

(30) Foreign Application Priority Data

Jun. 14, 2016 (EP) .................... 16305715

(51) Int. Cl.
C12Q 1/6883 (2018.01)
G16B 40/00 (2019.01)
C07K 16/24 (2006.01)

(52) U.S. Cl.
CPC .......... *C12Q 1/6883* (2013.01); *C07K 16/241* (2013.01); *G16B 40/00* (2019.02); *C07K 2317/24* (2013.01); *C12Q 2600/106* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

2013/0196335 A1* 8/2013 Avigad ............... C12Q 1/6886
435/6.14

FOREIGN PATENT DOCUMENTS

WO    2009/120877 A2    10/2009

OTHER PUBLICATIONS

Van der Goten et al. PLoS ONE 9(12): e116117, p. 1-26. (Year: 2014).*
Tumilson et al. Molecular Neurobiology. 2014. 50: 545-558 (Year: 2014).*
Tian et al PLOS One. Jan. 5, 2012. 7(1): e29551 (Year: 2012).*
Zhou et al Scientific Reports. Jun. 10, 2015. 6:11251 (Year: 2015).*
Wu et al Gastroenterology. 2008. 135: 1624-1635 (Year: 2008).*
Chen et al Biochem J. 2015. 471:357-367 (Year: 2015).*
Van Der Goten et al.; P055 "Integrated MiRNA and gene expression profiling in patients with ulcerative colitis before and after infliximab treatment"; Journal of Crohn's and Colitis, vol. 8, Feb. 1, 2014, pp. 585-586.

(Continued)

*Primary Examiner* — Carla J Myers
(74) *Attorney, Agent, or Firm* — W&C IP

(57) ABSTRACT

The present invention relates to methods for predicting acute severe colitis treatment response. Currently, there is no biomarker of drug response. The present invention provides the first prediction tool for responses to first- and second-line treatments in acute severe ulcerative colitis. Putative mRNA targets of dysregulated microRNAs were identified from patient biopsies. One classifier of fifteen colonic microRNAs plus five biological values at admission were identified with a prediction accuracy of 96.6% for discriminating responders from non-responders to steroids. Using a similar method, 6 and 4 mucosal microRNA-based algorithms were identified to classify responders from non-responders to infliximab and cyclosporine. In particular, the present invention relates to methods for predicting acute severe colitis treatment response by measuring the expression levels of several miRNAs selected from the group consisting of hp_hsa-mir-3934, hp_hsa-mir-100, hsa-miR-718, hp_hsa-mir-193b, hsa-miR-3150a-5p, hp_hsa-mir-1260b, hsa-miR-938, hsa-miR-518b and hsa-miR-1468.

4 Claims, No Drawings

(56) References Cited

OTHER PUBLICATIONS

Fujioka et al.; "Serum microRNA levels in patients with Crohn's disease during induction therapy by infliximab"; Journal of Gastroenterology and Hepatology, vol. 29, No. 6, Jun. 15, 2014, pp. 1207-1214.

Jiang et al.; "Molecular Analysis of Inflammatory Bowel Disease: Clinically Useful Tools for Diagnosis, Response Prediction, and Monitoring of Targeted Therapy"; Molecular Diagnosis and Therapy, vol. 19, No. 3, Jun. 1, 2015, pp. 141-158.

Naves et al.; DOP013 "Pre-treatment differential microRNA expression profile in ulcerative colitis patients according to their response to corticosteroids"; Journal of Crohn's and Colitis, vol. 8, Feb. 1, 2014, pp. 520-521.

\* cited by examiner

METHODS FOR PREDICTING ACUTE SEVERE COLITIS TREATMENT RESPONSE

FIELD OF THE INVENTION

The present invention relates to methods for predicting acute severe colitis treatment response.

BACKGROUND OF THE INVENTION

Ulcerative colitis (UC) is a lifelong, idiopathic chronic inflammatory disorder affecting the colorectal mucosa[1]. Approximately 15 to 25% of UC patients have had at least one episode of acute severe UC (ASUC). Such an episode is a life threatening condition and requires surgery, as it exposes patients to serious complications, including sepsis, toxic mega colon, colonic perforation, digestive bleeding and thromboembolic accidents [2, 3]. In patients who do not require emergency colectomy, intravenous (IV) corticosteroids are recommended as the first line of treatment [4]. However, 40% of patients will fail to respond to IV steroids [5, 6] and will require a salvage colectomy or second line treatment with cyclosporine (CsA) [7] or infliximab (IFX) [8] with good efficiency and safety [9]. In patients refractory to either of these two agents, an emergency colectomy is recommended instead of third-line medical therapy, as delayed surgery is associated with an increased mortality rate, estimated to be between 2 and 3%[10]. Thus, the treatment of ASUC requires an early assessment of the response to each medical treatment. However, physicians' decisions regarding treatment are currently based on the patient's evolution and a few clinical or biological parameters, such as Oxford criteria or Ho index, having low accuracy[11]. Then, relevant and early predictors of drug efficacy remain to be discovered. MicroRNAs (miRNAs) are short (21-25 nucleotides), non-coding RNA molecules that are most commonly transcribed by RNA III and processed by proteins, such as Drosha and Dicer[12]. MiRNAs have recently emerged as important mediators of immune development and response, suggesting their potential efficacy as biomarkers for diagnosis, determining prognosis and/or predicting treatment response in various diseases[13, 14]. In inflammatory bowel disease (IBD), such as UC, several studies have identified mucosal or blood miRNA signatures in both active and inactive patients[15], but no signatures have been identified yet for predicting drug response.

SUMMARY OF THE INVENTION

The present invention relates to methods for predicting acute severe colitis treatment response. In particular, the present invention is defined by the claims.

DETAILED DESCRIPTION OF THE INVENTION

Acute severe ulcerative colitis (ASUC) is a severe condition managed with intravenous steroids and infliximab or cyclosporine in the case of steroid resistance. If medical treatment fails, salvage colectomy would be delayed, which is associated with increased mortality. Currently, there is no biomarker of drug response; the aim was to identify predictors of responses to first- and second-line treatments in ASUC. Forty-seven patients with ASUC from two tertiary French units who were well characterized for their response to steroids, cyclosporine and infliximab were retrospectively included. The clinical and biological parameters were reviewed at admission. Fixed colonic biopsies taken before or within the first 3 days of treatment were used for microRNA expression profiling by microarray. Random forest-based classification algorithms were used to derive candidate biomarkers for discriminating responders from non-responders to each treatment and were calibrated through a leave-one-out cross validation. Putative mRNA targets of dysregulated microRNAs were identified. One classifier of 15 colonic microRNAs plus 5 biological values (haemoglobin, hematocrit, albumin, CRP, and transferrin expression levels) at admission were identified with a prediction accuracy of 96.6% (AUC=0.96) for discriminating responders from non-responders to steroids. Using a similar method, 6 and 4 mucosal microRNA-based algorithms were identified to classify responders from non-responders to infliximab (90%-AUC=0.86) and cyclosporine (83%-AUC=0.81), respectively. microRNA-related mRNA target analysis highlighted potential mucosal alterations associated with the drug response profile in ASUC. This study identified new predictors of responses to the first and second lines of treatment in patients with ASUC. The present invention thus provides a method for predicting drug response of subjects suffering from acute severe colitis (ASC). In particular, the present invention provides methods for predicting responses to a corticosteroid, an anti-TNFα drug and cyclosporine.

As used herein, the term "acute severe colitis" or "ASC" refers to acute severe colitis, a potentially lethal complication of ulcerative colitis (UC), an idiopathic, chronic inflammatory disorder affecting the colonic mucosa (K51-K52 such as revised in the World Health Organisation Classification). The term "acute severe colitis" also refers to acute severe ulcerative colitis. The acute severe colitis activity can be measured according to the standards recognized in the art. The acute severe colitis activity may be measured by clinical and physical examination, Lichtiger score and histological grading.

As used herein, the term "ASC treatment" refers to the typical medical regimen of acute severe colitis that includes a first line administration of a corticosteroid and a second line administration with an anti-TNFα drug (infliximab) and/or an immunosuppressive drug (cyclosporine).

As used herein, the term "corticosteroids" has its general meaning in the art and refers to the first line ASC treatment or first line ASC therapy. The term "corticosteroids" refers to first line administration of corticosteroids, the class of active ingredients having a hydrogenated cyclopentoperhydrophenanthrene ring system endowed with anti-inflammatory activity.

Corticosteroid drugs typically include cortisone, hydrocortisone, methylprednisolone, prednisone, prednisolone, betamethesone, beclomethasone dipropionate, budesonide, dexamethasone sodium phosphate, flunisolide, fluticasone propionate, triamcinolone acetonide, betamethasone, fluocinolone, fluocinonide, betamethasone dipropionate, betamethasone valerate, desonide, desoximetasone, fluocinolone, triamcinolone, triamcinolone acetonide, clobetasol propionate and dexamethasone.

As used herein, the term "anti-TNFα drug" is intended to encompass agents including proteins, antibodies, antibody fragments, fusion proteins (e.g., Ig fusion proteins or Fc fusion proteins), multivalent binding proteins (e.g., DVD Ig), small molecule TNFα antagonists and similar naturally- or non-naturally-occurring molecules, and/or recombinant and/or engineered forms thereof, that, directly or indirectly, inhibit TNFα activity, such as by inhibiting interaction of TNFα with a cell surface receptor for TNFα inhibiting TNFα protein production, inhibiting TNFα gene expression, inhibiting TNFα secretion from cells, inhibiting TNFα receptor signalling or any other means resulting in decreased TNFα activity in a subject. The term "anti-TNFα drug" preferably includes agents which interfere with TNFα activity. Examples of anti-TNFα drugs include, without limitation, infliximab (REMICADE™, Johnson and Johnson), human anti-TNF monoclonal antibody adalimumab (D2E7/HUMIRA™, Abbott Laboratories), etanercept (ENBREL™, Amgen), certolizumab pegol (CIMZIA®, UCB, Inc.), golimumab (SIMPONI®; CNTO 148), CDP 571 (Celltech), CDP 870 (Celltech), as well as other compounds which inhibit TNFα activity, such that when administered to a subject in which TNFα activity is detrimental, the disorder (i.e. acute severe colitis) could be treated.

As used herein, the term "cyclosporine" has its general meaning in the art and refers to an immunosuppressive drug. Cyclosporine (also named "cyclosporine A" or "CyA" was the cornerstone of rescue medical therapy for steroid-refractory acute severe colitis until the advent of anti-TNF agents. CyA is a competitive calcinuerin inhibitor with potent immunosuppressive properties.

As used herein, the term "responder" refers to an acute severe colitis (ASC) subject that will respond to ASC treatment. In a further aspect, the term "responder" refers to an acute severe colitis (ASC) subject that will respond to first line ASC treatment with corticosteroids. In a further aspect, the term "responder" refers to an acute severe colitis (ASC) subject that will respond to second line ASC treatment with anti-TNFα drug. In a further aspect, the term "responder" refers to an acute severe colitis (ASC) subject that will respond to second line ASC treatment with cyclosporine. In a further aspect, the term "responder" refers to an acute severe colitis (ASC) subject that will respond to second line ASC treatment with anti-TNFα drug and cyclosporine. The acute severe colitis activity can be measured according to the standards recognized in the art. The acute severe colitis activity may be measured by clinical and physical examination, Lichtiger score, histological grading and progression-free survival or overall survival. A "responder" or "responsive" subject to an acute severe colitis (ASC) treatment refers to a subject who shows or will show a clinically significant relief in the disease when treated with acute severe colitis (ASC) treatment.

The first object of the present invention ("object no 1") relates to a method of determining whether a subject suffering from acute severe colitis (ASC) will be a responder or a non-responder to a corticosteroid, comprising the steps of i) measuring in a mucosal tissue sample obtained from said subject before or during the first day of corticosteroid administration the expression level of at least one miRNA selected from the group consisting of hp_hsa-mir-3934, hp_hsa-mir-3667, hp_hsa-mir-100, hsa-miR-603, hsa-miR-718, hsa-miR-4259, hp_hsa-mir-193b, hsa-miR-3150a-5p, hp_hsa-mir-1260b, hsa-miR-938, hsa-miR-3128, hsa-miR-4423-3p, hsa-miR-518b, hsa-miR-1468 and hsa-miR-3152-3p, ii) comparing the expression level measured at step i) with a reference value, and iii) detecting differences in the expression level between the mucosal tissue sample and the reference value is indicative that said subject will be a responder or a non-responder.

In some embodiments, the expression level of 1, 2, 3, 4, 5, 6, 7, 8, 9, 10, 11, 12, 13, 14 or 15 miRNA selected from the group consisting of hp_hsa-mir-3934, hp_hsa-mir-3667, hp_hsa-mir-100, hsa-miR-603, hsa-miR-718, hsa-miR-4259, hp_hsa-mir-193b, hsa-miR-3150a-5p, hp_hsa-mir-1260b, hsa-miR-938, hsa-miR-3128, hsa-miR-4423-3p, hsa-miR-518b, hsa-miR-1468 and hsa-miR-3152-3p is determined. In some embodiments, the expression levels of hp_hsa-mir-3934, hp_hsa-mir-3667, hp_hsa-mir-100, hsa-miR-603, hsa-miR-718, hsa-miR-4259, hp_hsa-mir-193b, hsa-miR-3150a-5p, hp_hsa-mir-1260b, hsa-miR-938, hsa-miR-3128, hsa-miR-4423-3p, hsa-miR-518b, hsa-miR-1468 and hsa-miR-3152-3p are measured.

In some embodiments, the expressions levels of 9 miRNA are measured. Said 9 miRNA are hp_hsa-mir-3934, hp_hsa-mir-100, hsa-miR-718, hp_hsa-mir-193b, hsa-miR-3150a-5p, hp_hsa-mir-1260b, hsa-miR-938, hsa-miR-518b and hsa-miR-1468.

The second object of the present invention ("object no 2") relates to a method of determining whether a subject suffering from acute severe colitis (ASC) will be a responder or a non-responder to an anti-TNFα drug, comprising the steps of (i) measuring in a mucosal tissue sample obtained from said subject before or during the first days of anti-TNFα drug administration the expression level of at least one miRNA selected from the group consisting of hsa-miR-4423-3p, hsa-miR-3128, hsa-miR-3152-3p, hp_hsa-mir-193b, hsa-miR-938 and hp_hsa-mir-100, (ii) comparing the expression level measured at step i) with a reference value, and (iii) detecting differences in the expression level between the mucosal tissue sample and the reference value is indicative that said subject will be a responder or a non-responder.

In some embodiments, the expression level of 1, 2, 3, 4, 5 or 6 miRNA selected from the group consisting of hsa-miR-4423-3p, hsa-miR-3128, hsa-miR-3152-3p, hp_hsa-mir-193b, hsa-miR-938 and hp_hsa-mir-100 is determined. In some embodiments, the expression levels of hsa-miR-4423-3p, hsa-miR-3128, hsa-miR-3152-3p, hp_hsa-mir-193b, hsa-miR-938 and hp_hsa-mir-100 are determined.

In some embodiments, the expressions levels of 3 miRNA are measured. Said 3 miRNA are hp_hsa-mir-100, hsa-miR-938 and hsa-miR-518b.

The third object of the present invention ("object no 3") relates to a method of determining whether a subject suffering from acute severe colitis (ASC) will be a responder or a non-responder to cyclosporine, comprising the steps of i) measuring in a mucosal tissue sample obtained from said subject before or during the first days of cyclosporine administration the expression level of at least one miRNA selected from the group consisting of has-miR-4423-3p, has-miR-938, has-miR-518b and has-miR-100, ii) comparing the expression level measured at step i) with a reference value, and iii) detecting differences in the expression level between the mucosal tissue sample and the reference value is indicative that said subject will be a responder or a non-responder.

In some embodiments, the expression level of 1, 2, 3 or 4 miRNA selected from the group consisting of hsa-miR-4423-3p, hsa-miR-938, hsa-miR-518b and hsa-miR-100 is determined. In some embodiments, the expression levels of hsa-miR-4423-3p, hsa-miR-938, hsa-miR-518b and hsa-miR-100 are measured.

In some embodiments, the expressions levels of 3 miRNA are measured. Said 3 miRNA are hp_hsa-mir-100, hsa-miR-938 and hp_hsa-mir-193b.

The fourth object of the present invention ("object no 4") relates to a method of determining whether a subject suffering from acute severe colitis (ASC) will be a responder or a non-responder to a corticosteroid, anti-TNFα drug and cyclosporine by performing the methods of object 1, 2 and 3 as above described. In some embodiments, the methods of determining whether a subject suffering from acute severe colitis (ASC) will be a responder or a non-responder to a corticosteroid, anti-TNFα drug and cyclosporine are performed sequentially or concomitantly.

In some embodiments, the expressions levels of 9 miRNA are measured. Said 9 miRNA are hp_hsa-mir-3934, hp_hsa-mir-100, hsa-miR-718, hp_hsa-mir-193b, hsa-miR-3150a-5p, hp_hsa-mir-1260b, hsa-miR-938, hsa-miR-518b and hsa-miR-1468.

In some embodiments, the method of the invention comprises a step consisting of comparing the expression level of the miRNA with a reference value, wherein detecting differences in the expression level of the miRNA between the mucosal tissue sample and the reference value is indicative that said subject will be a responder or a non-responder.

A reference value is determined for each miRNA. Typically, the reference value can be a threshold value or a cut-off value. Typically, a "threshold value" or "cut-off value" can be determined experimentally, empirically, or theoretically. A threshold value can also be arbitrarily selected based upon the existing experimental and/or clinical conditions, as would be recognized by a person of ordinary skill in the art. The threshold value has to be determined in order to obtain the optimal sensitivity and specificity according to the function of the test and the benefit/risk balance (clinical consequences of false positive and false negative). Typically, the optimal sensitivity and specificity (and so the threshold value) can be determined using a Receiver Operating Characteristic (ROC) curve based on experimental data. Preferably, the person skilled in the art may compare the miRNAs expression levels (obtained according to the method of the invention with a defined threshold value). In one embodiment of the present invention, the threshold value is derived from the miRNA expression level (or ratio, or score) determined in a mucosal tissue sample derived from one or more subjects who are responders to a corticosteroid, anti-TNFα drug or cyclosporine. In one embodiment of the present invention, the threshold value may also be derived from the miRNA expression level (or ratio, or score) determined in a mucosal tissue sample derived from one or more subjects who are non-responders to a corticosteroid, anti-TNFα drug or cyclosporine. Furthermore, retrospective measurement of the miRNA expression levels (or ratio, or scores) in properly banked historical subject samples may be used in establishing these threshold values.

In some embodiments, the reference value may be determined by carrying out a method comprising the steps of a) providing a collection of mucosal tissue samples obtained from subjects before or during the first days of the corticosteroid treatment, b) providing, for each sample provided at step a), information relating to the actual clinical outcome (response or no response); c) providing a series of arbitrary quantification values; d) determining the level of the miRNA for each sample contained in the collection provided at step a); e) classifying said samples in two groups for one specific arbitrary quantification value provided at step c), respectively: (i) a first group comprising samples that exhibit a quantification value for the level that is lower than the said arbitrary quantification value contained in the said series of quantification values; (ii) a second group comprising samples that exhibit a quantification value for said level that is higher than the said arbitrary quantification value contained in the said series of quantification values; whereby two groups of samples are obtained for the said specific quantification value, wherein the samples of each group are separately enumerated; f) calculating the statistical significance between (i) the quantification value obtained at step e) and (ii) the actual clinical outcome of the subjects (i.e. response or non-response) from which samples contained in the first and second groups defined at step f) derive; g) reiterating steps f) and g) until every arbitrary quantification value provided at step d) is tested; and h) setting the said reference value as consisting of the arbitrary quantification value for which the highest statistical significance (most significant) has been calculated at step g).

For example, the level of the miRNA has been assessed for 100 samples of 100 subjects. The 100 samples are ranked according to the level of the miRNA. Sample 1 has the highest level and sample 100 has the lowest level. A first grouping provides two subsets: on one side sample Nr 1 and on the other side the 99 other samples. The next grouping provides on one side samples 1 and 2 and on the other side the 98 remaining samples etc., until the last grouping: on one side samples 1 to 99 and on the other side sample Nr 100. According to the information relating to the actual clinical outcome for the corresponding subjects, the p value between both subsets was calculated. The reference value is then selected such as the discrimination based on the criterion of the minimum p value is the strongest. In other terms, the level of the miRNA corresponding to the boundary between both subsets for which the p value is minimum is considered as the reference value. It should be noted that the reference value is not necessarily the median value of levels of the miRNA.

The setting of a single "cut-off" value thus allows discrimination between responder or non-responder. Practically, high statistical significance values (e.g. low P values) are generally obtained for a range of successive arbitrary quantification values, and not only for a single arbitrary quantification value. Thus, in one alternative embodiment of the invention, instead of using a definite reference value, a range of values is provided. Therefore, a minimal statistical significance value (minimal threshold of significance, e.g. maximal threshold P value) is arbitrarily set and a range of a plurality of arbitrary quantification values for which the statistical significance value calculated at step g) is higher (more significant, e.g. lower P value) are retained, so that a range of quantification values is provided. This range of quantification values includes a "cut-off" value as described above. For example, on a hypothetical scale of 1 to 10, if the ideal cut-off value (the value with the highest statistical significance) is 5, a suitable (exemplary) range may be from 4-6. Therefore, a subject may be assessed by comparing values obtained by measuring the level of the miRNA, where values greater than 5 reveal that the subject will be a responder (or alternatively a non-responder) and values less than 5 reveal that the subject will be a non-responder (or alternatively a responder). In another embodiment, a subject may be assessed by comparing values obtained by measuring the level of the miRNA and comparing the values on a scale, where values above the range of 4-6 indicate that the subject will be a responder (or alternatively a non-responder) and values below the range of 4-6 indicate that the subject will be a non-responder (or alternatively a non-responder), with values falling within the range of 4-6 indicating an intermediate response.

In some embodiments, a score which is a composite of the expression levels of the different miRNAs may also be determined and compared to a reference value wherein a difference between said score and said reference value is indicative whether said subject is a responder or a non-responder to corticosteroid, anti-TNFα drug or cyclosporine treatment.

In some embodiments, the method of the invention comprises the step of determining the subject response using a classification algorithm selected from Linear Discriminant Analysis (LDA), Topological Data Analysis (TDA), Neural Networks and Random Forests algorithm (RF) such as described in the Example. In some embodiments, the method of the invention comprises the step of determining the subject response using a classification algorithm wherein the classification algorithm is Deep learning classification. As used herein, the term "classification algorithm" has its general meaning in the art and refers to classification and regression tree methods and multivariate classification well known in the art such as described in U.S. Pat. No. 8,126,690; WO2008/156617. As used herein, the term "Random Forests algorithm" or "RF" has its general meaning in the art and refers to classification algorithm such as described in U.S. Pat. No. 8,126,690; WO2008/156617. Random Forest is a decision-tree-based classifier that is constructed using an algorithm originally developed by Leo Breiman (Breiman L, "Random forests," Machine Learning 2001, 45:5-32). The classifier uses a large number of individual decision trees and decides the class by choosing the mode of the classes as determined by the individual trees. The individual trees are constructed using the following algorithm: (1) Assume that the number of cases in the training set is N, and that the number of variables in the classifier is M; (2) Select the number of input variables that will be used to determine the decision at a node of the tree; this number, m should be much less than M; (3) Choose a training set by choosing N samples from the training set with replacement; (4) For each node of the tree randomly select m of the M variables on which to base the decision at that node; (5) Calculate the best split based on these m variables in the training set. In some embodiments, the score is generated by a computer program.

In some embodiments, a higher expression level of at least one miRNA selected from the group consisting of hsa-miR-4423-3p, hsa-miR-3128, hsa-miR-3152-3p and hsa-miR-603 and a lower expression level of at least one miRNA selected from the group consisting of hsa-miR-718, hsa-miR-4259, hp_hsa-mir-193b, hp_hsa-mir-3934, hp_hsa-mir-3667, hp_hsa-mir-1260b, hsa-miR-938, hsa-miR-3150a-5p, hp_hsa-mir-100, hsa-miR-518b and hsa-miR-1468 are indicative that the subject will be a responder to corticosteroid treatment, and accordingly a lower expression level of at least one miRNA selected from the group consisting of hsa-miR-4423-3p, hsa-miR-3128, hsa-miR-3152-3p and hsa-miR-603 and a higher expression level of at least one miRNA selected from the group consisting of hsa-miR-718, hsa-miR-4259, hp_hsa-mir-193b, hp_hsa-mir-3934, hp_hsa-mir-3667, hp_hsa-mir-1260b, hsa-miR-938, hsa-miR-3150a-5p, hp_hsa-mir-100, hsa-miR-518b and hsa-miR-1468 are indicative that the subject will be a non-responder to corticosteroid treatment.

In some embodiments, the reference value may correspond to the expression level determined in a mucosal tissue sample derived from one or more subjects who are responders to corticosteroid treatment. Accordingly, when the expression level determined for at least one miRNA selected from the group consisting of hsa-miR-4423-3p, hsa-miR-3128, hsa-miR-3152-3p and hsa-miR-603 is equal or higher than the corresponding reference value and/or the expression level of at least one miRNA selected from the group consisting of hsa-miR-718, hsa-miR-4259, hp_hsa-mir-193b, hp_hsa-mir-3934, hp_hsa-mir-3667, hp_hsa-mir-1260b, hsa-miR-938, hsa-miR-3150a-5p, hp_hsa-mir-100, hsa-miR-518b and hsa-miR-1468 is equal or lower than the corresponding reference value, it is concluded that the subject will be a responder to corticosteroid treatment, and accordingly, when the expression level determined for at least one miRNA selected from the group consisting of hsa-miR-4423-3p, hsa-miR-3128, hsa-miR-3152-3p and hsa-miR-603 is lower than the corresponding reference value and/or the expression level of at least one miRNA selected from the group consisting of hsa-miR-718, hsa-miR-4259, hp_hsa-mir-193b, hp_hsa-mir-3934, hp_hsa-mir-3667, hp_hsa-mir-1260b, hsa-miR-938, hsa-miR-3150a-5p, hp_hsa-mir-100, hsa-miR-518b and hsa-miR-1468 is higher than the corresponding reference value, its concluded that the subject will be a non-responder to corticosteroid treatment.

In some embodiments, the reference value may correspond to the expression level determined in a mucosal tissue sample derived from one or more subjects who are non-responders to corticosteroid treatment. Accordingly, when the expression level determined for at least one miRNA selected from the group consisting of hsa-miR-4423-3p, hsa-miR-3128, hsa-miR-3152-3p and hsa-miR-603 is higher than the corresponding reference value and/or the expression level of at least one miRNA selected from the group consisting of hsa-miR-718, hsa-miR-4259, hp_hsa-mir-193b, hp_hsa-mir-3934, hp_hsa-mir-3667, hp_hsa-mir-1260b, hsa-miR-938, hsa-miR-3150a-5p, hp_hsa-mir-100, hsa-miR-518b and hsa-miR-1468 is lower than the corresponding reference value, it is concluded that the subject will be a responder to corticosteroid treatment, and accordingly, when the expression level determined for at least one miRNA selected from the group consisting of hsa-miR-4423-3p, hsa-miR-3128, hsa-miR-3152-3p and hsa-miR-603 is equal or lower than the corresponding reference value and/or the expression level of at least one miRNA selected from the group consisting of hsa-miR-718, hsa-miR-4259, hp_hsa-mir-193b, hp_hsa-mir-3934, hp_hsa-mir-3667, hp_hsa-mir-1260b, hsa-miR-938, hsa-miR-3150a-5p, hp_hsa-mir-100, hsa-miR-518b and hsa-miR-1468 is equal or higher than the corresponding reference value, its concluded that the subject will be a non-responder to corticosteroid treatment.

In some embodiments, a higher expression level of at least one miRNA selected from the group consisting of hsa-miR-4423-3p, hsa-miR-3128 and hsa-miR-3152-3p and a lower expression level of at least one miRNA selected from the group consisting of hp_hsa-mir-193b, hsa-miR-938 and hp_hsa-mir-100 are indicative that the subject will be a responder to anti-TNFα drug treatment, and accordingly a lower expression level of at least one miRNA selected from the group consisting of hsa-miR-4423-3p, hsa-miR-3128 and hsa-miR-3152-3p and a higher expression level of at least one miRNA selected from the group consisting of hp_hsa-mir-193b, hsa-miR-938 and hp_hsa-mir-100 are indicative that the subject will be a non-responder to anti-TNFα drug treatment.

In some embodiments, the reference value may correspond to the expression level determined in a mucosal tissue sample derived from one or more subjects who are responders to anti-TNFα drug treatment. Accordingly, when the expression level determined for at least one miRNA selected from the group consisting of hsa-miR-4423-3p, hsa-miR-3128, and hsa-miR-3152-3p is equal or higher than the corresponding reference value and/or the expression level of at least one miRNA selected from the group consisting of hp_hsa-mir-193b, hsa-miR-938 and hp_hsa-mir-100 is equal or lower than the corresponding reference value, it is concluded that the subject will be a responder to anti-TNFα drug treatment, and accordingly, when the expression level determined for at least one miRNA selected from the group consisting of hsa-miR-4423-3p, hsa-miR-3128, and hsamiR-3152-3p is lower than the corresponding reference value and/or the expression level of at least one miRNA selected from the group consisting of hp_hsa-mir-193b, hsa-miR-938 and hp_hsa-mir-100 is higher than the corresponding reference value, its concluded that the subject will be a non-responder to anti-TNFα drug treatment.

In some embodiments, the reference value may correspond to the expression level determined in a mucosal tissue sample derived from one or more subjects who are non-responders to anti-TNFα drug treatment. Accordingly, when the expression level determined for at least one miRNA selected from the group consisting of hsa-miR-4423-3p, hsa-miR-3128, and hsa-miR-3152-3p is higher than the corresponding reference value and/or the expression level of at least one miRNA selected from the group consisting of hp_hsa-mir-193b, hsa-miR-938 and hp_hsa-mir-100 is lower than the corresponding reference value, it is concluded that the subject will be a responder to anti-TNFα drug treatment, and accordingly, when the expression level determined for at least one miRNA selected from the group consisting of hsa-miR-4423-3p, hsa-miR-3128, and hsa-miR-3152-3p is equal or lower than the corresponding reference value and/or the expression level of at least one miRNA selected from the group consisting of hp_hsa-mir-193b, hsa-miR-938 and hp_hsa-mir-100 is equal or higher than the corresponding reference value, its concluded that the subject will be a non-responder to anti-TNFα drug treatment.

In some embodiments, a higher expression level of miR-4423-3p and a lower expression level of at least one miRNA selected from the group consisting of hsa-miR-938, hsa-miR-518b and hsa-miR-100 are indicative that the subject will be a responder to cyclosporine treatment, and accordingly lower expression level of miR-4423-3p and higher expression level of at least one miRNA selected from the group consisting of hsa-miR-938, hsa-miR-518b and hsa-miR-100 are indicative that the subject will be a non-responder to cyclosporine treatment.

In some embodiments, the reference value may correspond to the expression level determined in a mucosal tissue sample derived from one or more subjects who are responders to cyclosporine treatment. Accordingly, when the expression level determined for miR-4423-3p is equal or higher than the corresponding reference value and/or the expression level of at least one miRNA selected from the group consisting of hsa-miR-938, hsa-miR-518b and hsa-miR-100 is equal or lower than the corresponding reference value, it is concluded that the subject will be a responder to cyclosporine treatment, and accordingly, when the expression level determined for hsa-miR-4423-3p is lower than the corresponding reference value and/or the expression level of at least one miRNA selected from the group consisting of hsa-miR-938, hsa-miR-518b and hsa-miR-100 is higher than the corresponding reference value, its concluded that the subject will be a non-responder to cyclosporine treatment.

In some embodiments, the reference value may correspond to the expression level determined in a mucosal tissue sample derived from one or more subjects who are non-responders to cyclosporine treatment. Accordingly, when the expression level determined for has-hsa-miR-4423-3p is higher than the corresponding reference value and/or the expression level of at least one miRNA selected from the group consisting of hsa-miR-938, hsa-miR-518b and hsa-miR-100 is lower than the corresponding reference value, it is concluded that the subject will be a responder to cyclosporine treatment, and accordingly, when the expression level determined for hsa-miR-4423-3p is equal or lower than the corresponding reference value and/or the expression level of at least one miRNA selected from the group consisting of hsa-miR-938, hsa-miR-518b and hsa-miR-100 is equal or higher than the corresponding reference value, its concluded that the subject will be a non-responder to cyclosporine treatment.

In some embodiments, the methods of the invention further comprises measuring at least one biological value selected from the group consisting of leukocyte, hematite, basophil and lymphocyte count, hematocrit, haemoglobin, glucose, ferritin, albumin, iron, C-reactive protein (CRP) and transferrin.

As used herein, the term "mucosal tissue sample" means any sample derived from the colon of the subject, which comprise mucosal cells. Said mucosal tissue sample may be obtained before or during the first day of the first line treatment with corticosteroids. Said mucosal tissue sample is obtained for the purpose of in vitro evaluation. In a particular embodiment the mucosal tissue sample results from an endoscopic biopsy performed in the colon of the subject. Said endoscopic biopsy may be taken from various areas of the colon. In another particular embodiment, the mucosal tissue sample may be isolated from inflamed mucosa of the subject's colon.

As used herein, the term "miR" has its general meaning in the art and refers to the miRNA sequence publicly available from the website data base located at microrna.sanger.ac.uk/sequences/ under the miRBase Accession number. The miRNAs pertaining to the invention are known per se, and are listed in the below Table A.

TABLE A

| list of the miRNAs biomarkers according to the invention | |
|---|---|
| miRNA | miRBase Accession number |
| hp_hsa-mir-3934 | MI0016590 |
| hp_hsa-mir-3667 | MI0016068 |
| hp_hsa-mir-100 | MI0000102 |
| hsa-miR-603 | MI0003616 |
| hsa-miR-718 | MI0012489 |
| hsa-miR-4259 | MI0015858 |
| hp_hsa-mir-193b | MI0003137 |
| hsa-miR-3150a-5p | MIMAT0019206 |
| hp_hsa-mir-1260b | MI0014197 |
| hsa-miR-938 | MI0005760 |
| hsa-miR-3128 | MI0014145 |
| hsa-miR-4423-3p | MIMAT0018936 |
| hsa-miR-518b | MI0003156 |
| hsa-miR-1468 | MI0003782 |
| hsa-miR-3152-3p | MIMAT0015025 |
| hsa-miR-3128 | MI0014145 |
| hp_hsa-mir-193b | MI0003137 |
| hsa-miR-4423-3p | MIMAT0018936 |

According to the invention, measuring the expression level of the miRNA selected from the group consisting of miRNAs of Table A of the invention in the mucosal tissue sample obtained from the subject can be performed by a variety of techniques. For example the nucleic acid contained in the samples (mucosal tissue prepared from the subject) is first extracted according to standard methods, for example using lytic enzymes or chemical solutions or extracted by nucleic-acid-binding resins following the manufacturer's instructions. Conventional methods and reagents for isolating RNA from a mucosal tissue sample comprise High Pure miRNA Isolation Kit (Roche), Trizol (Invitrogen), Guanidinium thiocyanate-phenol-chloroform extraction, PureLink™ miRNA isolation kit (Invitrogen), PureLink Micro-to-Midi Total RNA Purification System (invitrogen), RNeasy kit (Qiagen), miRNeasy kit (Qiagen), Oligotex kit (Qiagen), phenol extraction, phenol-chloroform extraction, TCA/acetone precipitation, ethanol precipitation, Column purification, Silica gel membrane purification, PureYield™ RNA Midiprep (Promega), PolyATtract System 1000 (Promega), Maxwell® 16 System (Promega), SV Total RNA Isolation (Promega), geneMAG-RNA/DNA kit (Chemicell), TRI Reagent® (Ambion), RNAqueous Kit (Ambion), ToTALLY RNA™ Kit (Ambion), Poly(A)Purist™ Kit (Ambion) and any other methods, commercially available or not, known to the skilled person. The expression level of one or more miRNA in the mucosal tissue sample may be determined by any suitable method. Any reliable method for measuring the level or amount of miRNA in a sample may be used. Generally, miRNA can be detected and quantified from a mucosal tissue sample (including fractions thereof), such as samples of isolated RNA by various methods known for mRNA, including, for example, amplification-based methods (e.g., Polymerase Chain Reaction (PCR), Real-Time Polymerase Chain Reaction (RT-PCR), Quantitative Polymerase Chain Reaction (qPCR), rolling circle amplification, etc.), hybridization-based methods (e.g., hybridization arrays (e.g., microarrays), NanoString analysis, Northern Blot analysis, branched DNA (bDNA) signal amplification, in situ hybridization, etc.), and sequencing-based methods (e.g., next-generation sequencing methods, for example, using the Illumina or IonTorrent platforms). Other exemplary techniques include ribonuclease protection assay (RPA) and mass spectroscopy.

In some embodiments, RNA is converted to DNA (cDNA) prior to analysis. cDNA can be generated by reverse transcription of isolated miRNA using conventional techniques. miRNA reverse transcription kits are known and commercially available. Examples of suitable kits include, but are not limited to the mirVana TaqMan® miRNA transcription kit (Ambion, Austin, Tex.), and the TaqMan® miRNA transcription kit (Applied Biosystems, Foster City, Calif.). Universal primers, or specific primers, including miRNA-specific stem-loop primers, are known and commercially available, for example, from Applied Biosystems. In some embodiments, miRNA is amplified prior to measurement. In some embodiments, the expression level of miRNA is measured during the amplification process. In some embodiments, the expression level of miRNA is not amplified prior to measurement. Some exemplary methods suitable for determining the expression level of miRNA in a sample are described in greater hereinafter. These methods are provided by way of illustration only, and it will be apparent to a skilled person that other suitable methods may likewise be used.

Many amplification-based methods exist for detecting the expression level of miRNA nucleic acid sequences, including, but not limited to, PCR, RT-PCR, qPCR, and rolling circle amplification. Other amplification-based techniques include, for example, ligase chain reaction (LCR), multiplex ligatable probe amplification, in vitro transcription (IVT), strand displacement amplification (SDA), transcription-mediated amplification (TMA), nucleic acid sequence based amplification (NASBA), RNA (Eberwine) amplification, and other methods that are known to persons skilled in the art. A typical PCR reaction includes multiple steps, or cycles, that selectively amplify target nucleic acid species: a denaturing step, in which a target nucleic acid is denatured; an annealing step, in which a set of PCR primers (i.e., forward and reverse primers) anneal to complementary DNA strands, and an elongation step, in which a thermostable DNA polymerase elongates the primers. By repeating these steps multiple times, a DNA fragment is amplified to produce an amplicon, corresponding to the target sequence. Typical PCR reactions include 20 or more cycles of denaturation, annealing, and elongation. In many cases, the annealing and elongation steps can be performed concurrently, in which case the cycle contains only two steps. A reverse transcription reaction (which produces a cDNA sequence having complementarity to a miRNA) may be performed prior to PCR amplification. Reverse transcription reactions include the use of, e.g., a RNA-based DNA polymerase (reverse transcriptase) and a primer. Kits for quantitative real time PCR of miRNA are known, and are commercially available. Examples of suitable kits include, but are not limited to, the TaqMan® miRNA Assay (Applied Biosystems) and the mirVana™ qRT-PCR miRNA detection kit (Ambion). The miRNA can be ligated to a single stranded oligonucleotide containing universal primer sequences, a polyadenylated sequence, or adaptor sequence prior to reverse transcriptase and amplified using a primer complementary to the universal primer sequence, poly(T) primer, or primer comprising a sequence that is complementary to the adaptor sequence. In some embodiments, custom qRT-PCR assays can be developed for determination of miRNA levels. Custom qRT-PCR assays to measure miRNAs in a sample can be developed using, for example, methods that involve an extended reverse transcription primer and locked nucleic acid modified PCR. Custom miRNA assays can be tested by running the assay on a dilution series of chemically synthesized miRNA corresponding to the target sequence. This permits determination of the limit of detection and linear range of quantitation of each assay. Furthermore, when used as a standard curve, these data permit an estimate of the absolute abundance of miRNAs measured in the samples. Amplification curves may optionally be checked to verify that Ct values are assessed in the linear range of each amplification plot. Typically, the linear range spans several orders of magnitude. For each candidate miRNA assayed, a chemically synthesized version of the miRNA can be obtained and analyzed in a dilution series to determine the limit of sensitivity of the assay, and the linear range of quantitation. Relative expression levels may be determined, for example, according to the 2($-\Delta\Delta$ C(T)) Method, as described by Livak et ah, Analysis of relative gene expression data using real-time quantitative PCR and the 2($-\Delta\Delta$ C(T)) Method. Methods (2001) December; 25(4):402-8.

In some embodiments, two or more miRNAs are amplified in a single reaction volume. For example, multiplex q-PCR, such as qRT-PCR, enables simultaneous amplification and quantification of at least two miRNAs of interest in one reaction volume by using more than one pair of primers and/or more than one probe. The primer pairs comprise at least one amplification primer that specifically binds each miRNA, and the probes are labeled such that they are distinguishable from one another, thus allowing simultaneous quantification of multiple miRNAs.

Rolling circle amplification is a DNA-polymerase driven reaction that can replicate circularized oligonucleotide probes with either linear or geometric kinetics under isothermal conditions (see, for example, Lizardi et al., Nat. Gen. (1998) 19(3):225-232; Gusev et al, Am. J. Pathol. (2001) 159(1):63-69; Nallur et al, Nucleic Acids Res. (2001) 29(23):E118). In the presence of two primers, one hybridizing to the (+) strand of DNA, and the other hybridizing to the (−) strand, a complex pattern of strand displacement results in the generation of over 109 copies of each DNA molecule in 90 minutes or less. Tandemly linked copies of a closed circle DNA molecule may be formed by using a single primer. The process can also be performed using a matrix-associated DNA. The template used for rolling circle amplification may be reverse transcribed. This method can be used as a highly sensitive indicator of miRNA sequence and expression level at very low miRNA concentrations (see, for example, Cheng et al., Angew Chem. Int. Ed. Engl. (2009) 48(18):3268-72; Neubacher et al, Chembiochem. (2009) 10(8): 1289-91).

miRNA quantification may be performed by using stem-loop primers for reverse transcription (RT) followed by a real-time TaqMan® probe. Typically, said method comprises a first step wherein the stem-loop primers are annealed to miRNA targets and extended in the presence of reverse transcriptase. Then miRNA-specific forward primer, TaqMan® probe, and reverse primer are used for PCR reactions. Quantitation of miRNAs is estimated based on measured CT values. Many miRNA quantification assays are commercially available from Qiagen (S. A. Courtaboeuf, France), Exiqon (Vedbaek, Denmark) or Applied Biosystems (Foster City, USA).

Expression levels of miRNAs may be expressed as absolute expression levels or normalized expression levels. Typically, expression levels are normalized by correcting the absolute expression level of miRNAs by comparing its expression to the expression of a mRNA that is not a relevant marker for determining whether a subject suffering from acute severe colitis (ASC) will be a responder or a non-responder to a corticosteroid, anti-TNFα drug and cyclosporine, e.g., a housekeeping mRNA that is constitutively expressed. Suitable mRNAs for normalization include housekeeping mRNAs such as the U6, U24, U48 and S18. This normalization allows the comparison of the expression level in one sample, e.g., a subject sample, to another sample, or between samples from different sources. In a particular embodiment, expression levels are normalized by correcting the absolute expression level of miRNAs by comparing its expression to the expression of a reference mRNA.

Nucleic acids exhibiting sequence complementarity or homology to the miRNAs of interest herein find utility as hybridization probes or amplification primers. It is understood that such nucleic acids need not be identical, but are typically at least about 80% identical to the homologous region of comparable size, more preferably 85% identical and even more preferably 90-95% identical. In certain embodiments, it will be advantageous to use nucleic acids in combination with appropriate means, such as a detectable label, for detecting hybridization. A wide variety of appropriate indicators are known in the art including, fluorescent, radioactive, enzymatic or other ligands (e. g. avidin/biotin).

The probes and primers are "specific" to the miRNAs they hybridize to, i.e. they preferably hybridize under high stringency hybridization conditions (corresponding to the highest melting temperature Tm, e.g., 50% formamide, 5× or 6×SCC. SCC is a 0.15 M NaCl, 0.015 M Na-citrate).

miRNA may be detected using hybridization-based methods, including but not limited to hybridization arrays (e.g., microarrays), NanoString analysis, Northern Blot analysis, branched DNA (bDNA) signal amplification, and in situ hybridization.

Microarrays can be used to measure the expression levels of large numbers of miRNAs simultaneously. Microarrays can be fabricated using a variety of technologies, including printing with fine-pointed pins onto glass slides, photolithography using pre-made masks, photolithography using dynamic micromirror devices, inkjet printing, or electrochemistry on microelectrode arrays. Also useful are microfluidic TaqMan Low-Density Arrays, which are based on an array of microfluidic qRT-PCR reactions, as well as related microfluidic qRT-PCR based methods. In one example of microarray detection, various oligonucleotides (e.g., 200+ 5'-amino-modified-C6 oligos) corresponding to human sense miRNA sequences are spotted on three-dimensional CodeLink slides (GE Health/Amersham Biosciences) at a final concentration of about 20 μM and processed according to manufacturer's recommendations. First strand cDNA synthesized from 20 μg TRIzol-purified total RNA is labeled with biotinylated ddUTP using the Enzo BioArray end labeling kit (Enzo Life Sciences Inc.). Hybridization, staining, and washing can be performed according to a modified Affymetrix Antisense genome array protocol. Axon B-4000 scanner and Gene-Pix Pro 4.0 software or other suitable software can be used to scan images. Non-positive spots after background subtraction, and outliers detected by the ESD procedure, are removed. The resulting signal intensity values are normalized to per-chip median values and then used to obtain geometric means and standard errors for each miRNA. Each miRNA signal can be transformed to log base 2, and a one-sample t test can be conducted. Independent hybridizations for each sample can be performed on chips with each miRNA spotted multiple times to increase the robustness of the data.

Microarrays can be used for the expression profiling of miRNAs. For example, RNA can be extracted from the sample and, optionally, the miRNAs are size-selected from total RNA. Oligonucleotide linkers can be attached to the 5' and 3' ends of the miRNAs and the resulting ligation products are used as templates for an RT-PCR reaction. The sense strand PCR primer can have a fluorophore attached to its 5' end, thereby labeling the sense strand of the PCR product. The PCR product is denatured and then hybridized to the microarray. A PCR product, referred to as the target nucleic acid that is complementary to the corresponding miRNA capture probe sequence on the array will hybridize, via base pairing, to the spot at which the capture probes are affixed. The spot will then fluoresce when excited using a microarray laser scanner. The fluorescence intensity of each spot is then evaluated in terms of the number of copies of a particular miRNA, using a number of positive and negative controls and array data normalization methods, which will result in assessment of the level of expression of a particular miRNA. Total RNA containing the miRNA extracted from the sample can also be used directly without size-selection of the miRNAs. For example, the RNA can be 3' end labeled using T4 RNA ligase and a fluorophore-labeled short RNA linker. Fluorophore-labeled miRNAs complementary to the corresponding miRNA capture probe sequences on the array hybridize, via base pairing, to the spot at which the capture probes are affixed. The fluorescence intensity of each spot is then evaluated in terms of the number of copies of a particular miRNA, using a number of positive and negative controls and array data normalization methods, which will result in assessment of the level of expression of a particular miRNA. Several types of microarrays can be employed including, but not limited to, spotted oligonucleotide microarrays, pre-fabricated oligonucleotide microarrays or spotted long oligonucleotide arrays.

Accordingly, the nucleic acid probes include one or more labels, for example to permit detection of a target nucleic acid molecule using the disclosed probes. In various applications, such as in situ hybridization procedures, a nucleic acid probe includes a label (e.g., a detectable label). A "detectable label" is a molecule or material that can be used to produce a detectable signal that indicates the presence or concentration of the probe (particularly the bound or hybridized probe) in a sample. Thus, a labeled nucleic acid molecule provides an indicator of the presence or concentration of a target nucleic acid sequence (e.g., genomic target nucleic acid sequence) (to which the labeled uniquely specific nucleic acid molecule is bound or hybridized) in a sample. A label associated with one or more nucleic acid molecules (such as a probe generated by the disclosed methods) can be detected either directly or indirectly. A label can be detected by any known or yet to be discovered mechanism including absorption, emission and/or scattering of a photon (including radio frequency, microwave frequency, infrared frequency, visible frequency and ultraviolet frequency photons). Detectable labels include colored, fluorescent, phosphorescent and luminescent molecules and materials, catalysts (such as enzymes) that convert one substance into another substance to provide a detectable difference (such as by converting a colorless substance into a colored substance or vice versa, or by producing a precipitate or increasing sample turbidity), haptens that can be detected by antibody binding interactions, and paramagnetic and magnetic molecules or materials.

Particular examples of detectable labels include fluorescent molecules (or fluorochromes). Numerous fluorochromes are known to those of skill in the art, and can be selected, for example from Life Technologies (formerly Invitrogen), e.g., see, The Handbook-A Guide to Fluorescent Probes and Labeling Technologies). Examples of particular fluorophores that can be attached (for example, chemically conjugated) to a nucleic acid molecule (such as a uniquely specific binding region) are provided in U.S. Pat. No. 5,866,366 to Nazarenko et al., such as 4-acetamido-4'-isothiocyanatostilbene-2,2' disulfonic acid, acridine and derivatives such as acridine and acridine isothiocyanate, 5-(2'-aminoethyl) aminonaphthalene-1-sulfonic acid (EDANS), 4-amino-N-[3 vinylsulfonyl)phenyl]naphthalimide-3,5 disulfonate (Lucifer Yellow VS), N-(4-anilino-1-naphthyl)maleimide, Brilliant Yellow, coumarin and derivatives such as coumarin, 7-amino-4-methylcoumarin (AMC, Coumarin 120), 7-amino-4-trifluoromethylcoumarin (Coumarin 151); cyanosine; 4',6-diarninidino-2-phenylindole (DAPI); 5',5"dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), Dichlorotriazinylamino fluorescein (DTAF), 2'7'dimethoxy-4'5'-dichloro-6-carboxyfluorescein (JOE), fluorescein, fluorescein isothiocyanate (FITC), and QFITC Q(RITC); 2',7'-difluorofluorescein (OREGON GREEN®); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, rhodamine green, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives. Other suitable fluorophores include thiol-reactive europium chelates which emit at approximately 617 mn (Heyduk and Heyduk, Analyt. Biochem. 248:216-27, 1997; J. Biol. Chem. 274:3315-22, 1999), as well as GFP, Lissamine™, diethylaminocoumarin, fluorescein chlorotriazinyl, naphthofluorescein, 4,7-dichlororhodamine and xanthene (as described in U.S. Pat. No. 5,800,996 to Lee et al.) and derivatives thereof. Other fluorophores known to those skilled in the art can also be used, for example those available from Life Technologies (Invitrogen; Molecular Probes (Eugene, Oreg.)) and including the ALEXA FLUOR® series of dyes (for example, as described in U.S. Pat. Nos. 5,696,157, 6, 130, 101 and 6,716,979), the BODIPY series of dyes (dipyrrometheneboron difluoride dyes, for example as described in U.S. Pat. Nos. 4,774,339, 5,187,288, 5,248,782, 5,274,113, 5,338, 854, 5,451,663 and 5,433,896), Cascade Blue (an amine reactive derivative of the sulfonated pyrene described in U.S. Pat. No. 5,132,432) and Marina Blue (U.S. Pat. No. 5,830,912).

In addition to the fluorochromes described above, a fluorescent label can be a fluorescent nanoparticle, such as a semiconductor nanocrystal, e.g., a QUANTUM DOT™ (obtained, for example, from Life Technologies (QuantumDot Corp, Invitrogen Nanocrystal Technologies, Eugene, Oreg.); see also, U.S. Pat. Nos. 6,815,064; 6,682,596; and 6,649, 138). Semiconductor nanocrystals are microscopic particles having size-dependent optical and/or electrical properties. When semiconductor nanocrystals are illuminated with a primary energy source, a secondary emission of energy occurs of a frequency that corresponds to the bandgap of the semiconductor material used in the semiconductor nanocrystal. This emission can he detected as colored light of a specific wavelength or fluorescence. Semiconductor nanocrystals with different spectral characteristics are described in e.g., U.S. Pat. No. 6,602,671. Semiconductor nanocrystals that can he coupled to a variety of biological molecules (including dNTPs and/or nucleic acids) or substrates by techniques described in, for example, Bruchez et al., Science 281:20132016, 1998; Chan et al., Science 281: 2016-2018, 1998; and U.S. Pat. No. 6,274,323. Formation of semiconductor nanocrystals of various compositions are disclosed in, e.g., U.S. Pat. Nos. 6,927,069; 6,914,256; 6,855,202; 6,709,929; 6,689,338; 6,500,622; 6,306,736; 6,225,198; 6,207,392; 6,114,038; 6,048,616; 5,990,479; 5,690,807; 5,571,018; 5,505,928; 5,262,357 and in U.S. Patent Publication No. 2003/0165951 as well as PCT Publication No. 99/26299 (published May 27, 1999). Separate populations of semiconductor nanocrystals can he produced that are identifiable based on their different spectral characteristics. For example, semiconductor nanocrystals can he produced that emit light of different colors based on their composition, size or size and composition. For example, quantum dots that emit light at different wavelengths based on size (565 nm, 655 nm, 705 nm, or 800 nm emission wavelengths), which are suitable as fluorescent labels in the probes disclosed herein are available from Life Technologies (Carlsbad, Calif.).

RT-PCR is typically carried out in a thermal cycler with the capacity to illuminate each sample with a beam of light of a specified wavelength and detect the fluorescence emitted by the excited fluorophore. The thermal cycler is also able to rapidly heat and chill samples, thereby taking advantage of the physicochemical properties of the nucleic acids and thermal polymerase. The majority of the thermocyclers on the market now offer similar characteristics. Typically, thermocyclers involve a format of glass capillaries, plastics tubes, 96-well plates or 384-well plates. The thermocylcer also involves software analysis.

miRNAs can also be detected without amplification using the nCounter Analysis System (NanoString Technologies, Seattle, Wash.). This technology employs two nucleic acid-based probes that hybridize in solution (e.g., a reporter probe and a capture probe). After hybridization, excess probes are removed, and probe/target complexes are analyzed in accordance with the manufacturer's protocol. nCounter miRNA assay kits are available from NanoString Technologies, which are capable of distinguishing between highly similar miRNAs with great specificity. The basis of the nCounter® Analysis system is the unique code assigned to each nucleic acid target to be assayed (International Patent Application Publication No. WO 08/124847, U.S. Pat. No. 8,415,102 and Geiss et al. Nature Biotechnology. 2008. 26(3): 317-325; the contents of which are each incorporated herein by reference in their entireties). The code is composed of an ordered series of colored fluorescent spots which create a unique barcode for each target to be assayed. A pair of probes is designed for each oligonucleotide target, a biotinylated capture probe and a reporter probe carrying the fluorescent barcode. This system is also referred to, herein, as the nanoreporter code system. Specific reporter and capture probes are synthesized for each target. The reporter probe can comprise at a least a first label attachment region to which are attached one or more label monomers that emit light constituting a first signal; at least a second label attachment region, which is non-over-lapping with the first label attachment region, to which are attached one or more label monomers that emit light constituting a second signal; and a first target-specific sequence. Preferably, each sequence specific reporter probe comprises a target specific sequence capable of hybridizing to no more than one gene and optionally comprises at least three, or at least four label attachment regions, said attachment regions comprising one or more label monomers that emit light, constituting at least a third signal, or at least a fourth signal, respectively. The capture probe can comprise a second target-specific sequence; and a first affinity tag. In some embodiments, the capture probe can also comprise one or more label attachment regions. Preferably, the first target-specific sequence of the reporter probe and the second target-specific sequence of the capture probe hybridize to different regions of the same gene to be detected. Reporter and capture probes are all pooled into a single hybridization mixture, the "probe library". The relative abundance of each target is measured in a single multiplexed hybridization reaction. The method comprises contacting the sample with a probe library, such that the presence of the target in the sample creates a probe pair—target complex. The complex is then purified. More specifically, the sample is combined with the probe library, and hybridization occurs in solution. After hybridization, the tripartite hybridized complexes (probe pairs and target) are purified in a two-step procedure using magnetic beads linked to oligonucleotides complementary to universal sequences present on the capture and reporter probes. This dual purification process allows the hybridization reaction to be driven to completion with a large excess of target-specific probes, as they are ultimately removed, and, thus, do not interfere with binding and imaging of the sample. All post hybridization steps are handled robotically on a custom liquid-handling robot (Prep Station, NanoString Technologies). Purified reactions are typically deposited by the Prep Station into individual flow cells of a sample cartridge, bound to a streptavidin-coated surface via the capture probe, electrophoresed to elongate the reporter probes, and immobilized. After processing, the sample cartridge is transferred to a fully automated imaging and data collection device (Digital Analyzer, NanoString Technologies). The expression level of a target is measured by imaging each sample and counting the number of times the code for that target is detected. For each sample, typically 600 fields-of-view (FOV) are imaged (1376×1024 pixels) representing approximately 10 mm2 of the binding surface. Typical imaging density is 100-1200 counted reporters per field of view depending on the degree of multiplexing, the amount of sample input, and overall target abundance. Data is output in simple spreadsheet format listing the number of counts per target, per sample. This system can be used along with nanoreporters. Additional disclosure regarding nanoreporters can be found in International Publication No. WO 07/076129 and WO07/076132, and US Patent Publication No. 2010/0015607 and 2010/0261026, the contents of which are incorporated herein in their entireties. Further, the term nucleic acid probes and nanoreporters can include the rationally designed (e.g. synthetic sequences) described in International Publication No. WO 2010/019826 and US Patent Publication No. 2010/0047924, incorporated herein by reference in its entirety.

Mass spectroscopy can be used to quantify miRNA using RNase mapping. Isolated RNAs can be enzymatically digested with RNA endonucleases (RNases) having high specificity (e.g., RNase Tl, which cleaves at the 3'-side of all unmodified guanosine residues) prior to their analysis by MS or tandem MS (MS/MS) approaches. The first approach developed utilized the on-line chromatographic separation of endonuclease digests by reversed phase HPLC coupled directly to ESTMS. The presence of post-transcriptional modifications can be revealed by mass shifts from those expected based upon the RNA sequence. Ions of anomalous mass/charge values can then be isolated for tandem MS sequencing to locate the sequence placement of the post-transcriptionally modified nucleoside. Matrix-assisted laser desorption/ionization mass spectrometry (MALDI-MS) has also been used as an analytical approach for obtaining information about post-transcriptionally modified nucleosides. MALDI-based approaches can be differentiated from EST-based approaches by the separation step. In MALDI-MS, the mass spectrometer is used to separate the miRNA. To analyze a limited quantity of intact miRNAs, a system of capillary LC coupled with nanoESI-MS can be employed, by using a linear ion trap-orbitrap hybrid mass spectrometer (LTQ Orbitrap XL, Thermo Fisher Scientific) or a tandem-quadrupole time-of-flight mass spectrometer (QSTAR® XL, Applied Biosystems) equipped with a custom-made nanospray ion source, a Nanovolume Valve (Valco Instruments), and a splitless nano HPLC system (DiNa, KYA Technologies). Analyte/TEAA is loaded onto a nano-LC trap column, desalted, and then concentrated. Intact miRNAs are eluted from the trap column and directly injected into a CI 8 capillary column, and chromatographed by RP-HPLC using a gradient of solvents of increasing polarity. The chromatographic eluent is sprayed from a sprayer tip attached to the capillary column, using an ionization voltage that allows ions to be scanned in the negative polarity mode.

Additional methods for miRNA detection and measurement include, for example, strand invasion assay (Third Wave Technologies, Inc.), surface plasmon resonance (SPR), cDNA, MTDNA (metallic DNA; Advance Technologies, Saskatoon, SK), and single-molecule methods such as the one developed by US Genomics. Multiple miRNAs can be detected in a microarray format using a novel approach that combines a surface enzyme reaction with nanoparticle-amplified SPR imaging (SPRI). The surface reaction of poly(A) polymerase creates poly(A) tails on miRNAs hybridized onto locked nucleic acid (LNA) microarrays. DNA-modified nanoparticles are then adsorbed onto the poly(A) tails and detected with SPRI. This ultrasensitive nanoparticle-amplified SPRI methodology can be used for miRNA profiling at attamole levels. miRNAs can also be detected using branched DNA (bDNA) signal amplification (see, for example, Urdea, Nature Biotechnology (1994), 12:926-928). miRNA assays based on bDNA signal amplification are commercially available. One such assay is the QuantiGene® 2.0 miRNA Assay (Affymetrix, Santa Clara, Calif.). Northern Blot and in situ hybridization may also be used to detect miRNAs. Suitable methods for performing Northern Blot and in situ hybridization are known in the art. Advanced sequencing methods can likewise be used as available. For example, miRNAs can be detected using Illumina® Next Generation Sequencing (e.g. Sequencing-By-Synthesis or TruSeq methods, using, for example, the HiSeq, HiScan, GenomeAnalyzer, or MiSeq systems (Illumina, Inc., San Diego, Calif.)). miRNAs can also be detected using Ion Torrent Sequencing (Ion Torrent Systems, Inc., Gulliford, Conn.), or other suitable methods of semi-conductor sequencing.

A further object relates to a kit for performing the methods of the present invention, wherein said kit comprises means for measuring the expression level of at least one miRNA selected from miRNAs of Table A that is indicative of subject responder to corticosteroid, anti-TNFα drug or cyclosporine treatment. Typically the kit may include primers, probes macroarrays or microarrays as above described. For example, the kit may comprise a set of miRNA probes as above defined, usually made of DNA, and optionally pre-labelled. Alternatively, probes may be unlabelled and the ingredients for labelling may be included in the kit in separate containers. The kit may further comprise hybridization reagents or other suitably packaged reagents and materials needed for the particular hybridization protocol, including solid-phase matrices, if applicable, and standards. Alternatively the kit of the invention may comprise amplification primers (e.g. stem-loop primers) that may be pre-labelled or may contain an affinity purification or attachment moiety. The kit may further comprise amplification reagents and also other suitably packaged reagents and materials needed for the particular amplification protocol.

The methods of the invention thus allow to define a subgroup of subjects who will be responders or non-responders to corticosteroid, anti-TNFα drug or cyclosporine treatment.

Accordingly a further object the present invention relates to a method of treating acute severe colitis (ASC) by a corticosteroid in a subject in need thereof comprising the steps of a) determining whether the subject will be a responder or a non-responder to a corticosteroid by performing the method according to object no 1, and b) administering the corticosteroid, if said subject has been considered as a responder in step a).

A further object of the present invention relates to a method of treating acute severe colitis (ASC) by an anti-TNFα drug in a subject in need thereof comprising the steps of a) determining whether the subject will be a responder or a non-responder to anti-TNFα drug by performing the method according to object no 2, and b) administering the anti-TNFα drug, if said subject has been considered as a responder in step a).

A further object of the present invention relates to a method of treating acute severe colitis (ASC) by cyclosporine in a subject in need thereof comprising the steps of a) determining whether the subject will be a responder or a non-responder to cyclosporine by performing the method according object no 3, and b) administering the cyclosporine, if said subject has been considered as a responder in step a).

A further object of the present invention relates to a method of treating acute severe colitis (ASC) by a corticosteroid, an anti-TNFα drug, cyclosporine or colectomy in a subject in need thereof comprising the steps of a) determining whether the subject will be a responder or a non-responder to a corticosteroid, anti-TNFα drug, and cyclosporine by performing the method according object no 4, and b) administering the corticosteroid, if said subject has been considered as a responder to the corticosteroid in step a), c) administering the anti-TNFα drug, if said subject has been considered as a non-responder to the corticosteroid and as a responder to anti-TNFα drug in step a), d) administering cyclosporine, if said subject has been considered as a non-responder to the corticosteroid and as a responder to cyclosporine in step a), and e) performing a colectomy, if said subject has been considered as a non-responder to the corticosteroid, anti-TNFα drug and cyclosporine in step a).

As used herein, the term "colectomy" refers to surgical resection of any extent of the large intestine (colon). Herein, colectomy includes, but is not limited to right hemicolectomy, left hemicolectomy, extended hemicolectomy, transverse colectomy, sigmoidectomy, proctosigmoidectomy, Hartmann operation, "double-barrel" or Mikulicz colostomy, total colectomy (also known as Lane's Operation), total procto-colectomy and subtotal colectomy.

In some embodiments, the method of the invention comprises the step of administering the anti-TNFα drug and cyclosporine, if the subject has been considered as a non-responder to the corticosteroid, as a responder to the anti-TNFα drug and as a responder to cyclosporine by performing the method according to the invention.

The invention will be further illustrated by the following Example. However, this example should not be interpreted in any way as limiting the scope of the present invention.

EXAMPLE

Material & Methods
Patients:
Patients were selected from two French tertiary centres: Beaujon Hospital (Assistance Publique des Hôpitaux de Paris) and Haut-Lévêque (CHU de Bordeaux) Hospital. The institutional review boards of both centres approved this study, and all patients were informed. The selection of patients was retrospectively made from clinical files and pathological databases. The inclusion criteria were the following: older than 18 years of age, well-established UC diagnosis according to ECCO criteria[16], admission for an ASUC episode based on a Lichtiger index above 10 points at admission[17], and flexible recto-sigmoidoscopy with colonic biopsies performed within 5 days following admission. Colonic biopsies were taken at admission or during the first days of IV steroid treatment before the assessment of the clinical response to this treatment at days 3 to 5. The exclusion criteria were the following: having Crohn's disease, absence of biopsies at entry or insufficient RNA amount (less than 5 ng/μl), and follow-up duration of less than 3 months after admission for ASUC. Patients were recruited from January 2007 to October 2014, including 11 patients previously included in the CYSIF study, which compared CsA to IFX as second-line medical therapy for steroid refractory ASUC [9]. In both centres, patients received IV steroids (at least 0.8 mg/kg/d of methylprednisolone) as the first-line therapy. In patients with an insufficient response after 3 to 5 days, second-line treatment with CsA or IFX was started in patients who did not require a colectomy according to clinical need and experienced physician advice. CsA was started at 2 mg/kg/day and was subsequently adapted according to blood concentrations to obtain levels of 150 to 250 ng/mL. IFX was infused at the usual dose of 5 mg/kg at weeks 0, 2, and 6 and was continued as maintenance therapy. Thiopurine was offered to all patients responding to steroids, IFX or CsA. For each treatment, the treatment response definitions used were those from the CYSIF trial. Treatment failure was defined by one or more of the following conditions: absence of a clinical response at day 7, defined by a Lichtiger index above 10 points; relapse before month 3, defined by a Lichtiger index of greater than 10 or of more than 3 points on three consecutive days; need for a new systemic UC therapy; or colectomy or death within 3 months of starting treatment. Conversely, treatment success was defined by a Lichtiger index of less than 10 points without any failure criteria on at least 2 consecutive days within the first week of treatment.

RNA Extraction

Biopsies analysed in the study were all taken from inflamed mucosa of the sigmoid colon. Total RNA was extracted from formaldehyde fixed and paraffin embedded (FFPE) tissue (seven 10-μm sections cut with a microtome from FFPE tissue blocks) using a RecoverAll™ Total Nucleic Acid kit (Ambion®, Life Technologies™). The FFPE samples were deparaffinized using a series of xylene and ethanol washes and then subjected to a rigorous protease digestion. Nucleic acids were purified using a rapid glass-fibre filter methodology, which includes an on-filter DNAse treatment, and then eluted into water. The purity and amount of total RNA extracted were assessed with a spectrophotometer (Nanodrop™ Spectrophotometer). All samples had a 260/280 ratio above 1.6.

microRNA Assessment

The expression level of human pre- and mature miRNAs was assessed using GeneChip® miRNA4.0 Arrays (Affymetrix, Santa Clara, USA) with 100% coverage of the mirBASE v20 listed microRNAs. An amount of 70 ng of total RNA was biotin labelled using the FlashTag Biotin HSR RNA labelling kit (Affymetrix). Briefly, we started with poly(A) tailing followed by ligation of the biotinylated signal molecule to the target RNAs in the sample. After overnight hybridization, chips were washed on a fluidic station FS450 following specific protocols (Affymetrix) and scanned using the GCS3000 7G. The scanned images were then analysed with Expression Console software (Affymetrix) to obtain raw data (CEL files) and metrics for Quality Controls. The observations of some of these metrics and the study of the distribution of raw data showed no outliers. Then, the hybridization data (CEL files) were normalized by a miRNA QC tool and filtered by flags (absent or present). The raw array data was analysed by an unpaired t-test.

Differential microRNA Signature Expression Analysis

To measure the similarity between steroid and CsA/IFX responders and non-responders for the 3,391-miRNA expression profiles, we modelled data using general linear models adopted from the R package 'Limma'[19]. At this stage, neither the "responders" nor "non-responders" labels were considered for the construction of the matrix. The first set of 24 miRNA candidates was chosen from the top-ranking candidates based on the false discovery rate (fdr<0.05). Subsequently, annotated heatmaps were produced using the R package 'Heatplus' [20]. Additionally, we developed a blended strategy to characterize predictive biomarkers, integrating patient features based on inferences from patient data, i.e., miRNA expression levels plus biological indicators. This approach is built on two complementary actions: (1) refining the previous set of features integrating a non-supervised enquiry for knowledge related to particular miRNAs and (2) integrating a list of key medically relevant clinical indicators.

Prediction Analysis

Classification Algorithms and Cross Validation Methods

The biological profile obtained from initial biopsies was used to predict the response to first- and second-line ASUC medical treatments. The classification of samples from responders or non-responders was assessed through an assorted set of methods, including Linear Discriminant Analysis (LDA), Topological Data Analysis (TDA, [21]) Neural Networks or the Random Forest algorithm (RF). However, a tailored deep learning model (DL, [** at the bottom]) outperformed the other methods and showed more statistical robustness in the two cohort studies. Regarding method validation, the Leave-One-Out cross-validation (LOO, [23]) approach was used on each sample. In these computations, we iteratively accounted for two performance functions: (1) the Sum Squared Error performance function (SSE), and (2) a classification score consisting of the following formula: [Σerror/(sample size)]×100. Whereas the classification score is used as a rough estimate of the statistical power for the RF classification method, we leveraged SSE to calculate the coefficient of variation (CV) in our prediction algorithm. Notice that CV is concerned with the model fit in terms of the relative sizes of the squared residuals (SSE) and outcome values.

Analysis of Prediction Accuracy

The performance of each DL drug classification was analysed by means of its receiver operating characteristic (ROC) curve. We also wanted to validate our feature selection method using a cross-procedure similar to that described in the previous section. Thus, when a patient was removed from the list of candidates during the LOO cross-validation, the feature selection method was run without the patient, and we ranked the 15 and the 9 miRNAs produced by this process in both the discovery and the validation cohorts respectively. Therefore, when making a prediction on an out-of-sample patient, we did not use his data during the feature selection process nor during the training of the classification algorithm.

Target Prediction and Pathway Analysis

To determine how the putative regulatory targets of the selected differentially expressed miRNAs alter biological pathways, a mapping of our predictive biomarker candidates was applied against four different databases in two different groups, namely: (1) KEGG and Reactome ([24,25]) against Targetscan[26] and miRBase[27]; (2) mirPath[28] against microT-CDS[29] and TarBase[30]. A hypergeometric test mathematically evaluated each gene set enrichment related to deregulated functions or pathways. Similar to the target analysis of the selected miRNAs, we evaluated the mature miRNAs and regions of the miRNAs in the target genes in a particular KEGG or Reactome Gene Ontology (GO)[31] category or pathway.

Results:

Patients

Forty-seven patients with ASUC have been included. For 10 patients, ASUC was their first occurrence of UC. All patients presented severe clinical and biological signs of colitis, with a mean Lichtiger index of 13.4 points and a mean C-reactive protein (CRP) level of 60.3 mg/l. All of the patients had Mayo endoscopic subscore of 3, including 11 with deep ulcerations. Briefly, 14 patients responded to the first line of IV steroids, and most were further treated with thiopurines. Thirty-three patients were resistant to steroids and required a second or third line of treatment. Among these 33 patients, 24 received IFX, 15 received CsA, and 6 received both drugs. Thus, 12 patients responded and 12 failed to respond to IFX. Additionally, 9 patients responded and 6 patients failed to respond to CsA. In steroid non-responders, 10 patients underwent a colectomy during follow-up.

MicroRNA Expression Profile

Discovery Cohort

We measured the expression of 3,391 human microRNAs in colonic biopsies fixed in FFPE from 47 patients admitted for an episode of ASUC. The FFPE colonic biopsies were obtained from the inflamed mucosa of 35 patients before the IV steroid treatment. Twelve patients had colonic biopsies within the first 3 days of the IV steroid course. Unsupervised clustering analysis showed 24 initial miRNA candidates, clearly separating steroid responders from non-responders. We further applied an integrative method for feature selection to reduce the signature. A set of 15 miRNAs was selected: hp_hsa-mir-3934, hp_hsa-mir-3667, hp_hsa-mir-100, hsa-miR-603, hsa-miR-718, hsa-miR-4259, hp_hsa-mir-193b, hsa-miR-3150a-5p, hp_hsa-mir-1260b, hsa-miR-938, hsa-miR-3128, hsa-miR-4423-3p, hsa-miR-518b, hsa-miR-1468 and hsa-miR-3152-3p. In the steroid-non-responders group, we evaluated the value of using miRNAs to discriminate between second-line therapy responders and non-responders whose biopsies were obtained before (or during) the first line of steroid treatment. Following the previous selection methodology, we identified 6 (hsa-miR-4423-3p, hsa-miR-3128, hsa-miR-3152-3p, hp_hsa-mir-193b, hsa-miR-938) and 4 miRNAs (hsa-miR-4423-3p, hsa-miR-938, hsa-miR-518b and hsa-miR-100) associated with response to IFX and CsA, respectively. The miRNAs that were differentially expressed in second-line treatment responders vs non-responders were included in the set of 15 miRNAs associated with steroid response.

Validation Cohort

We measured by qPCR analysis the expression of the 15 selected human miRNAs in colonic biopsies fixed in FFPE from 29 additional patients with similar inclusion criteria recruited secondarily. 9 out of the 15 miRNAs were expressed and remained as candidates: hp_hsa-mir-3934, hp_hsa-mir-100, hsa-miR-718, hp_hsa-mir-193b, hsa-miR-3150a-5p, hp_hsa-mir-1260b, hsa-miR-938, hsa-miR-518b and hsa-miR-1468. Next, we evaluated these 9 miRNAs candidates in the discrimination between steroids responders and non-responders to the validation cohort (data not shown). 3 miRNAs were associated with response to IFX and CsA (data not shown).

Deep Learning Classification

Several classification methods were applied to develop a miRNA classifier for steroid, IFX and CsA, responders versus non-responders. Among them, we selected the deep learning (DL) method, whose performance was the best both for the discovery and the validation cohorts. This selection was made based on the raw and CV scores (see methods) before the LOO validation. In turn, DL performing multi-classification with 2 categorical features, 14 numerical levels and expecting to have 33 input neurons yielded the best results. Upon the use of feature selection, as described in the Methods section, the classifiers for the discovery cohort were the 15-miRNA steroid response, 6-miRNA IFX response and 4-miRNA CsA response and 9-miRNA steroid response, 3-miRNA IFX response and 3-miRNA CsA for the validation cohort. At this stage, the intrinsic risk of overfitting, as we picked 15-9, 6-3 or 4-3 miRNAs out of 3,391, is worth noting. For that reason, we developed a feature selection strategy based only on unsupervised biological enquiries and integrated this feature selection strategy into the LOO cross-validation strategy afterwards. Furthermore, the classifiers were combined with some biological data (see further below), achieving classification success levels of ~94%, 90% and ~83% between responders and non-responders to steroids, IFX and CsA in the discovery cohort. And ~90%, ~84% and ~80% between responders and non-responders to steroids, IFX and CsA in the validation cohort.

Adding Biological Data to Improve Classification Value Stability

To improve the stratification strategy, we added values from biological sample types collected at the same time as the biopsy to the miRNA signature in a semi-supervised fashion. Sample types included leukocytes, haematites, haematocrit, haemoglobin, glucose, ferritin, transferrin, albumin, iron, basophil and lymphocyte counts and C-reactive protein (CRP) levels. Importantly, prognostic values for the steroid response were improved by combining the selected miRNAs and a non-linear transformation of 5 clinically relevant biological parameters (haemoglobin, haematocrit, albumin, CRP, and transferrin levels). Hence, the DL stratification algorithm steroid response prediction performance (see FIG. 4 and table 2) increased to an ~97%/~93% level of success for the discovery cohort and the validation cohort respectively. However, no combination of biological values allowed us to improve the IFX and CsA response classifiers.

Cross Validation

The parameter leveraged to mathematically validate our predictors was the CV, which was used as an exponent of the goodness exhibited by our strategy and a raw score of classification. Thus, from this score, a thorough analysis of each DL drug classification was performed according to their associated ROC curves (FIG. 4), i.e., $AUC_{steroids}$=0.92-0.96/0.83-0.91 (without or with biological indicators inclusion) for the discovery and validation cohorts, $AUC_{IFX}$=0.86 and $AUC_{CsA}$=0.81. The CV values for the steroid, IFX and CsA, classifier performances were 0.03-0.01 (without/with biological indicators), 0.05 and 0.08 (see Table 2). The benchmarking of the unsupervised feature selection method showed similar prognostic values in each run (data not shown).

Discussion:

To our knowledge, the present study is one of the first to establish a miRNA-based biomarker for precision medicine in IBD. The identification of predictors of clinical outcomes is a major challenge in ASUC treatment. Several scores have been established to predict pejorative clinical outcomes after starting steroid treatment for ASUC. Travis et al. determined that on day 3 of intravenous treatment, the treatment for patients with more than eight stools on that day, or a stool frequency between three and eight with a CRP above 45 mg/l, would fail [18]. Seo et al. proposed a composite activity index (60×blood stool+13×bowel movements+0.5× erythrocyte sedimentation rate−4×haemoglobin−15×albumin+200) [19]. In the pilot study, remission occurred in all patients with ASUC, as indicated by an index below 180 points 2 weeks after therapy, whereas approximately 65% of patients with an index above 180 points subsequently required a colectomy[20]. A recent study from the IBD UK audit analysed the value of the Travis and the Ho indexes to predict steroid failure in a retrospective cohort of 420 patients with ASUC[11]. High-risk patients in Travis and the Ho groups, when compared to lower risk groups, were more likely to fail steroid therapy: 64.5% vs. 38.7% ((P<0.0001) for Travis and 66.2% vs. 46.7% vs. 36.6% (P<0.0001) for Ho[11]. These results highlight the limited value of these indexes to stratify responders vs non-responders to steroids.

More recently, biological indicators have been correlated with ASUC clinical outcomes. Ho et al. showed that faecal calprotectin was significantly higher in patients who required a colectomy [21]. In a paediatric cohort of ASUC, an elevated faecal M2-pyruvate kinase level was associated with steroid response [22]. However, the Pediatric UC Activity Index, a simple clinical index, performed better than the faecal markers in predicting outcomes following a course of intravenous steroids in ASUC.

Despite many efforts, there are currently no accurate predictors of responses to treatments in ASUC. In a paediatric cohort of 79 patients with ASUC, the interleukine-6 (IL-6) plasma level at day 3 of an IV steroid course was significantly different between responders and non-responders [23]. However, in multivariate analysis, IL-6 was not associated with the steroid response, suggesting an association with disease activity rather than with steroid pathway failure [23]. The G2677T/A polymorphism (TT genotype) of the multidrug resistance gene (MDR1) was associated with the risk of CsA failure in a cohort of 154 patients with steroid resistant episodes of ASUC [24]. However, this genetic marker was neither validated nor used in daily practice. Mucosal expression of TNF-alpha was inversely associated with endoscopic and clinical responses to IFX in UC [25]. The same group also determined that high expression levels of IL-17A and IFN-γ were significantly associated with remission after three IFX infusions (OR=5.4, p=0.013 and OR=5.5, p=0.011, respectively) [26]. More recently, faecal loss of IFX was associated with IFX failure in ASUC and severe colonic Crohn's disease [27].

A simple score predicting standard drug responses is still lacking in treating patients with ASUC. For this reason, miRNAs were considered to be relevant candidates. Dysregulation of a specific subset of miRNAs has been identified in several studies performed on inflammatory or quiescent colonic mucosa of patients with UC[28]. An abnormal expression of several miRNAs was similarly identified in several independent studies. These miRNAs were mostly identified in inflammatory colonic mucosa, suggesting their participation in dysregulated inflammatory processes (miR-21-5p, miR-155-5p, miR-146a-5p, miR-31-5p, etc.). Interestingly, in other diseases, mostly cancers, some miRNAs have been studied for their potential prognostic values. To our knowledge, microRNA-based prognostic biomarkers have still not been established for IBD management.

To build this prediction algorithm, we established a retrospective, bicentric, well-defined cohort of patients with UC who were admitted for an episode of ASUC. Treatment procedures, evaluations and definitions of responses or relapses were strictly defined according to the CYSIF randomized trial criterion[9]. Even the different clinical outcomes and drug response profiles of the patients included were characterized retrospectively. The predictive nature of the algorithm results from the fact that the biochemical and molecular signatures were obtained before or during the first days of initial treatment. Twelve patients had their biopsies taken during the first line of IV steroids. Their signatures of the 15 selected miRNAs were not affected in comparison with those naïve IV steroids patients (data not shown).

Overall, this predictive algorithm utilizes a mathematical approach that goes beyond a simple miRNA signature. It uses a stratification tool using the DL layer of neurons decision method whereby multiple comparisons are made between the individual data of a patient (mucosal expression of 15-9 microRNAs, plus five biological values for steroids) and those of a matrix of patients who are well characterized for their responses to defined treatments. Thus, for each patient tested in the algorithm, one obtains a probability of their response to IV steroids, IFX and CsA by learning a non-linear equation that properly captures the set of solutions of a system composed by 9 miRNAs expression in qPCR and 5 biological indicators whose qualitative behaviour resembles in norm the treatment output. Our approach, in addition to identifying a limited set of response drivers, enables the improvement of the performance ranges of classification methods, such as the classic logistic regression from outreaches, of ~80% to ~93% (~97% with biological data), even when the entire set of miRNAs is taken into consideration. Unlike other similar studies recently published [29], our method addressed a small number of patients. To face this limit, the novelty of the proposed predictive algorithm is not only built on a signature of mucosal miRNAs but on a versatile method with: (1) a purely unsupervised feature selection phase to minimize over-fitting issues, (2) a classification task using random forests algorithm, and (3) the addition of biological data to improve efficiency. In particular, we do not rely on differential expression or random forest variables for selecting the best miRNAs, as in Li et al. [29]. Instead, our selection approach relies on a combination of unsupervised feature selection by hierarchical clustering and integrative data analysis by matching the identified miRNAs with existing biological knowledge. This integration with external knowledge enhances the performance of unsupervised feature selection in the context of a small number of patients. As far as the classification task is concerned, we leverage the random forest algorithm (not the centroid algorithm used in [29]), which was calibrated with a leave-one-out cross-validation due to the limited number of patients. Of note, the 5 biological data types were helpful in predicting responses to steroids, but not second line treatment responses, as these data were collected at admission.

Interestingly, the presence of deep ulcerations on pre-therapeutic endoscopy assessment was not associated with the prediction of the drug response profile, and this item was not retained in the final DL predictive algorithm.

In summary, our study provides the first prediction tool for responses to first- and second-line treatments in ASUC. Our results are encouraging for the development of predictive medicine in UC, even if they must be validated prospectively.

REFERENCES

Throughout this application, various references describe the state of the art to which this invention pertains. The disclosures of these references are hereby incorporated by reference into the present disclosure.

1 Ordas I, Eckmann L, Talamini M, et al. Ulcerative colitis. Lancet 2012; 380:1606-19.
2 Edwards F C, Truelove S C. The Course and Prognosis of Ulcerative Colitis. Gut 1963; 4:299-315.

3 Grainge M J, West J, Card T R. Venous thromboembolism during active disease and remission in inflammatory bowel disease: a cohort study. *Lancet* 2010; 375:657-63.
4 Truelove S C, Jewell D P. Intensive intravenous regimen for severe attacks of ulcerative colitis. *Lancet* 1974; 1:1067-70.
5 Truelove S C, Witts L J. Cortisone in ulcerative colitis; preliminary report on a therapeutic trial. *Br Med J* 1954; 2:375-8.
6 D'Haens G, Lemmens L, Geboes K, et al. Intravenous cyclosporine versus intravenous corticosteroids as single therapy for severe attacks of ulcerative colitis. *Gastroenterology* 2001; 120:1323-9.
7 Van Assche G, D'Haens G, Noman M, et al. Randomized, double-blind comparison of 4 mg/kg versus 2 mg/kg intravenous cyclosporine in severe ulcerative colitis. *Gastroenterology* 2003; 125:1025-31.
8 Jarnerot G, Hertervig E, Friis-Liby I, et al. Infliximab as rescue therapy in severe to moderately severe ulcerative colitis: a randomized, placebo-controlled study. *Gastroenterology* 2005; 128:1805-11.
9 Laharie D, Bourreille A, Branche J, et al. Ciclosporin versus infliximab in patients with severe ulcerative colitis refractory to intravenous steroids: a parallel, open-label randomised controlled trial. *Lancet* 2012; 380:1909-15.
10 Randall J, Singh B, Warren B F, et al. Delayed surgery for acute severe colitis is associated with increased risk of postoperative complications. *Br J Surg* 2010; 97:404-9.
11 Lynch R W, Churchhouse A M, Protheroe A, et al. Predicting outcome in acute severe ulcerative colitis: comparison of the Travis and Ho scores using UK IBD audit data. *Aliment Pharmacol Ther* 2016; 43:1132-41.
12 Winter J, Jung S, Keller S, et al. Many roads to maturity: microRNA biogenesis pathways and their regulation. *Nat Cell Biol* 2009; 11:228-34.
13 Nana-Sinkam S P, Croce C M. Clinical applications for microRNAs in cancer. *Clin Pharmacol Ther* 2013; 93:98-104.
14 Simpson L J, Ansel K M. MicroRNA regulation of lymphocyte tolerance and autoimmunity. *J Clin Invest* 2015; 125:2242-9.
15 Kalla R, Ventham N T, Kennedy N A, et al. MicroRNAs: new players in IBD. *Gut* 2015; 64:504-17.
16 Dignass A, Eliakim R, Magro F, et al. Second European evidence-based consensus on the diagnosis and management of ulcerative colitis part 1: definitions and diagnosis. *J Crohns Colitis* 2012; 6:965-90.
17 Lichtiger S, Present D H, Kornbluth A, et al. Cyclosporine in severe ulcerative colitis refractory to steroid therapy. *N Engl J Med* 1994; 330:1841-5.
18 Travis S P, Farrant J M, Ricketts C, et al. Predicting outcome in severe ulcerative colitis. *Gut* 1996; 38:905-10.
19 Seo M, Okada M, Yao T, et al. An index of disease activity in patients with ulcerative colitis. *Am J Gastroenterol* 1992; 87:971-6.
20 Seo M, Okada M, Yao T, et al. Evaluation of the clinical course of acute attacks in patients with ulcerative colitis through the use of an activity index. *J Gastroenterol* 2002; 37:29-34.
21 Ho G T, Lee H M, Brydon G, et al. Fecal calprotectin predicts the clinical course of acute severe ulcerative colitis. *Am J Gastroenterol* 2009; 104:673-8.
22 Turner D, Leach S T, Mack D, et al. Faecal calprotectin, lactoferrin, M2-pyruvate kinase and S100A12 in severe ulcerative colitis: a prospective multicentre comparison of predicting outcomes and monitoring response. *Gut* 2010; 59:1207-12.
23 Wine E, Mack D R, Hyams J, et al. Interleukin-6 is associated with steroid resistance and reflects disease activity in severe pediatric ulcerative colitis. *J Crohns Colitis* 2013; 7:916-22.
24 Daniel F, Loriot M A, Seksik P, et al. Multidrug resistance gene-1 polymorphisms and resistance to cyclosporine A in patients with steroid resistant ulcerative colitis. *Inflamm Bowel Dis* 2007; 13:19-23.
25 Olsen T, Goll R, Cui G, et al. TNF-alpha gene expression in colorectal mucosa as a predictor of remission after induction therapy with infliximab in ulcerative colitis. *Cytokine* 2009; 46:222-7.
26 Rismo R, Olsen T, Cui G, et al. Mucosal cytokine gene expression profiles as biomarkers of response to infliximab in ulcerative colitis. *Scand J Gastroenterol* 2012; 47:538-47.
27 Brandse J F, van den Brink G R, Wildenberg M E, et al. Loss of Infliximab Into Feces Is Associated With Lack of Response to Therapy in Patients With Severe Ulcerative Colitis. *Gastroenterology* 2015; 149:350-5 e2.
28 Van der Goten J, Vanhove W, Lemaire K, et al. Integrated miRNA and mRNA expression profiling in inflamed colon of patients with ulcerative colitis. *PLoS One* 2014; 9:e116117.
29 Li J, Chen Z, Tian L, et al. LncRNA profile study reveals a three-lncRNA signature associated with the survival of patients with oesophageal squamous cell carcinoma. *Gut* 2014; 63:1700-10.
**Deng, L.; Yu, D. (2014). "Deep Learning: Methods and Applications". *Foundations and Trends in Signal Processing*. 7 (3-4): 1-199. doi:10.1561/2000000039.

The invention claimed is:

1. A method of treating acute severe colitis (ASC) in a subject who has ASC, comprising
   i) administering a corticosteroid to the subject;
   ii) measuring, in a mucosal tissue sample obtained from the subject, before the step of administering and/or during at least the first five days of corticosteroid administration, the expression levels of hsa-miR-4423-3p, hsa-miR-3128, hsa-miR3152-3p, hsa-miR-603, hsa-miR-718, hp-hsa-mir-4259, hp_hsa-mir-193b, hp_hsa-mir-3934, hp-hsa-mir-3667, hp_hsa-mir-1260b, hsa-miR-938, hsa-miR-3150a-5p, hp_hsa-mir-100, hsa-miR-518b and hsa-miR-1468 miRNAs;
   iii) detecting a higher expression level of each of hsa-miR-4423-3p, hsa-miR-3128, hsa-miR3152-3p and hsa-miR-603, and a lower expression level of each of hsa-miR-718, hp-hsa-mir-4259, hp_hsa-mir-193b, hp_hsa-mir-3934, hp-hsa-mir-3667, hp_hsa-mir-1260b, hsa-miR-938, hsa-miR-3150a-5p, hp_hsa-mir-100, hsa-miR-518b and hsa-miR-1468, compared to a reference value, in combination with the level of hemoglobin, hematocrit, albumin, C-reactive protein and transferrin expression, as indicative that a subject will be responsive to the corticosteroid; and
   iv) administering the corticosteroid to the subject who will be responsive to the corticosteroid.

2. The method of claim 1 wherein the corticosteroid is methylprednisolone.

3. The method of claim 1, wherein the expression levels of the miRNAs are compared to the reference value using a classification algorithm selected from deep learning classification, Linear Discriminant Analysis (LDA), Topological Data Analysis (TDA), Neural Networks and Random Forests algorithm (RF).

4. The method of claim 1, further comprising a step of measuring at least one biological value selected from the group consisting of leukocyte, hematite, basophil and lymphocyte count, glucose, ferritin, and iron.

* * * * *